United States Patent
Forster et al.

(10) Patent No.: US 7,580,500 B2
(45) Date of Patent: Aug. 25, 2009

(54) COMPUTER TOMOGRAPHY SYSTEM HAVING A RING-SHAPED STATIONARY X-RAY SOURCE ENCLOSING A MEASURING FIELD

(75) Inventors: Jan Forster, Ingolstadt (DE); Reinhold Müller, Marloffstein (DE)

(73) Assignee: Jan and Renate Forster, Ingolstadt (DE)

( * ) Notice: Subject to any disclaimer, the term of this patent is extended or adjusted under 35 U.S.C. 154(b) by 51 days.

(21) Appl. No.: 11/829,222

(22) Filed: Jul. 27, 2007

(65) Prior Publication Data
US 2008/0137805 A1    Jun. 12, 2008

(30) Foreign Application Priority Data

| Jul. 28, 2006 | (DE) | ........................ 10 2006 035 742 |
| Oct. 20, 2006 | (DE) | ........................ 10 2006 049 630 |
| Apr. 20, 2007 | (DE) | ........................ 10 2007 019 176 |

(51) Int. Cl.
*H01J 35/30* (2006.01)
*H05G 1/52* (2006.01)
*G01N 23/083* (2006.01)

(52) U.S. Cl. .................... 378/10; 378/98.6; 378/113; 378/137

(58) Field of Classification Search ............... 378/10, 378/98.6, 113, 137
See application file for complete search history.

(56) References Cited

U.S. PATENT DOCUMENTS

| 4,158,142 A | 6/1979 | Haimson |
| 4,531,226 A | 7/1985 | Peschmann |
| 4,631,741 A * | 12/1986 | Rand et al. ..................... 378/10 |
| 5,172,401 A * | 12/1992 | Asari et al. .................... 378/10 |
| 5,247,556 A * | 9/1993 | Eckert et al. .................... 378/4 |
| 5,490,193 A | 2/1996 | Kuroda et al. |
| 5,504,791 A * | 4/1996 | Hell et al. ..................... 378/10 |
| 5,548,630 A * | 8/1996 | Hell et al. .................... 378/137 |
| 5,995,586 A * | 11/1999 | Jahnke ........................ 378/10 |
| 7,068,749 B2 | 6/2006 | Kollegal et al. |

(Continued)

FOREIGN PATENT DOCUMENTS

| DE | 42 10 339 A1 | 12/1992 |
| DE | 196 21 066 A1 | 11/1997 |
| DE | 195 15 415 A1 | 11/1998 |

OTHER PUBLICATIONS

German Patent Office Search Report, May 31, 2007.

*Primary Examiner*—Edward J Glick
*Assistant Examiner*—Thomas R Artman
(74) *Attorney, Agent, or Firm*—Dority & Manning, P.A.

(57) ABSTRACT

A computer tomograph (1) that comprises at least a stationary electron source for generating an electron beam (13), a ring-shaped, stationary X-ray source with a largely ring-shaped target (14) enclosing a measuring field (7), media for coaxially guiding (22) the electron beam (13) in the X-ray source (5) along a circular path to the ring-shaped target (14), as well as media for deflecting (21) the electron beam (13) towards the target (14), in order to generate an X-ray cluster (8) that rotates concentrically around itself for irradiating the measuring field (7) from various directions. Furthermore, the computer tomograph (1) comprises a stationary detector (6) executed as a ring shape and consisting of numerous detector elements from which a computer calculates the measured values to create an image of the examined object in the measuring field (7). The ring-shaped target (14) has numerous discrete focal areas (20) that can be scanned discontinuously by a focal point of the electron beam (13').

30 Claims, 7 Drawing Sheets

U.S. PATENT DOCUMENTS

| | | | |
|---|---|---|---|
| 7,203,269 B2 * | 4/2007 | Huber et al. | 378/10 |
| 7,233,644 B1 * | 6/2007 | Bendahan et al. | 378/57 |
| 7,280,631 B2 * | 10/2007 | De Man et al. | 378/10 |
| 2006/0002515 A1 | 1/2006 | Huber et al. | |
| 2008/0056436 A1 * | 3/2008 | Pack et al. | 378/10 |
| 2008/0056437 A1 * | 3/2008 | Pack et al. | 378/10 |

* cited by examiner

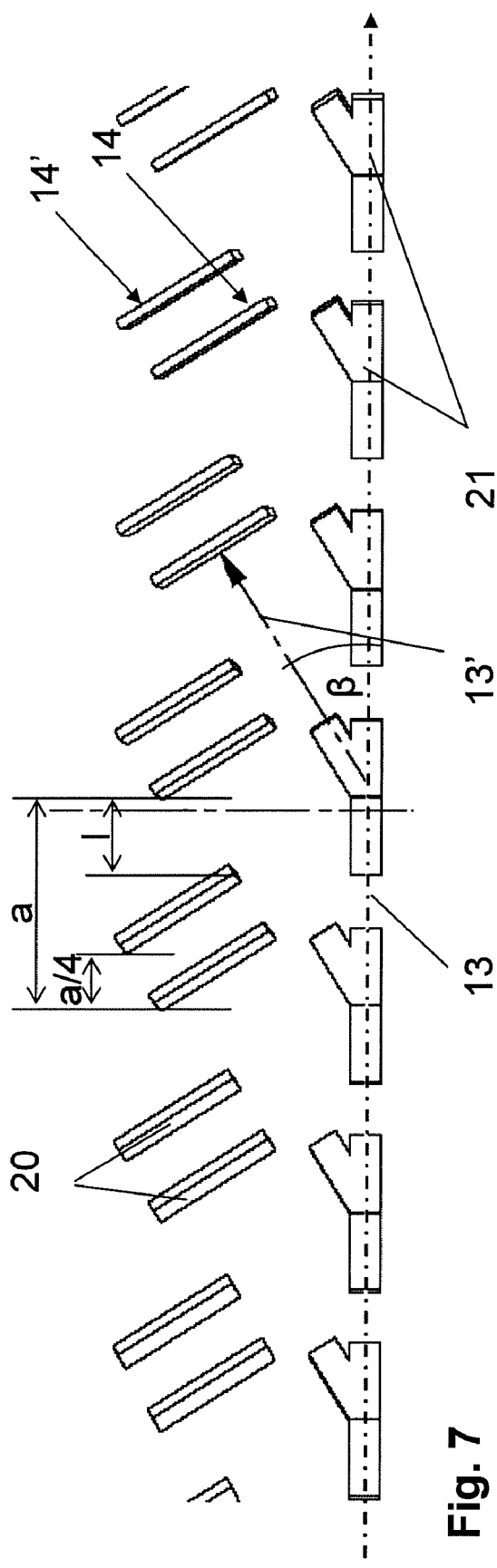
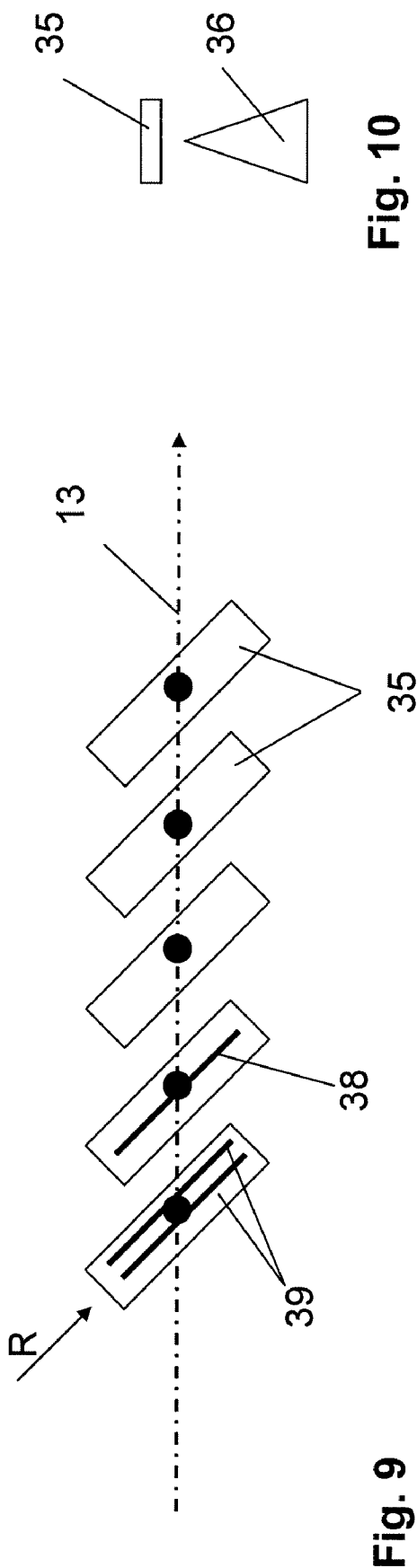
Fig. 7
Fig. 9
Fig. 10

COMPUTER TOMOGRAPHY SYSTEM HAVING A RING-SHAPED STATIONARY X-RAY SOURCE ENCLOSING A MEASURING FIELD

FIELD OF THE INVENTION

The present invention refers to a computer tomograph that comprises at least a stationary electron source for generating an electron beam and a ring-shaped, enclosing stationary X-ray source with a largely ring-shaped target, with media to coaxially guide the electron beam in the X-ray source along a circular path to the ring-shaped target, as well as media to deflect the electron beam towards the target. As a result of this, a concentrically rotating X-ray bundle is generated from different directions for irradiating the measuring field. The computer tomograph comprises also a developed, ring-shaped stationary detector consisting of multiple detector elements from whose measured readings the computer calculates an image of the object being examined in the measuring field.

BACKGROUND

State-of-the-art computer tomography units are known in many executions. The overwhelming majority of units being used include a rotating X-ray tube and a rotating detector ring. The energy and data transfer from the rotating parts takes place via slip rings. As a result of this and the high centrifugal forces that occur in the parts rotating around the object being measured, scanning times can only be shortened in a very limited way.

Furthermore, other units are already known in which the mechanical components no longer move. Such a computer tomography unit is described in DE 42 10 339 A1, for example. In that patent, the computer tomography unit is created by a largely ring-shaped structure in which an electron beam rotates ring-wise in a vacuum container. Furthermore, a ring-shaped anode has been arranged in the ring-shaped structure. The electron beam is guided to a circular path by electron beam guidance media and deflected towards the anode with the help of extraction media. Both the electron beam's circular path and the anode ring have a coaxial and coplanar design, but arranged on different diameters. In this case, the anode has been executed as a continuous anode ring that is continuously being scanned by the focused electron beam.

The task of the present invention is to suggest a computer tomograph that will offer an improved image quality with less radiation exposure.

SUMMARY

Objects and advantages of the invention will be set forth in part in the following description, or may be obvious from the description, or may be learned through practice of the invention A computer tomograph is made up of at least one stationary electron source for generating an electron beam and a ring-shaped, enclosing stationary X-ray source located in the measuring field with one largely ring-shaped target, and media in the X-ray source to coaxially guide the electron beam towards a circular path to the ring-shaped target as well as media for deflecting the electron beam towards the target. Furthermore, the computer tomograph comprises a ring-shaped developed stationary detector made up of numerous detector elements. The impact of the deflected electron beam on the target generates a concentrically rotating X-ray bundle for irradiating the measuring field from various directions. A computer calculates an image of the object being examined from the measured values of the individual elements of the detector. According to the invention, the ring-shaped target has many discrete focal areas that can be discontinuously scanned by a focal point of the electron beam.

Contrary to conventional computer tomography units, in which the focus continuously strikes over the target or anode surface, and a medium stopping place on the target or anode area is allocated to it (in which case a slightly smudged image is created), the computer tomograph according to the present invention works with discrete focal areas and discontinuous scanning by the focal point of the electron beam. This discreteness makes it possible to allocate in each case the radiation measured in the detector elements to an exact spot on the focal area. As a result of this, multiple still images with better image quality are created. At the same time, the exact allocation makes it possible to lower radiation exposure with identical or even better image quality compared to units having the same technical advances.

It is advantageous if the target has a stepped annular structure with saw tooth elements whose division corresponds at least to a 2° division of the full circle. This facilitates the allocation of many discrete focal areas on one target ring. In this case, the number of steps in the target ring largely determines image definition. In case of a 1° division, the target has 361 steps, but more precise gradations with 721 steps are also possible, for example. Here, it is advantageous for the number of steps to be an odd number, since in that case the number of independent projections can be doubled.

A further development of the invention recommends the target to be made up of many individual elements, each one arranged on a saw tooth element of the stepped ring-shaped carrier. This arrangement makes it possible to reduce the quantity of the relatively expensive target material to a minimum and to manufacture the carrier from a suitable, more economical material. In this case, the carrier can form one piece together with a beam delivery tube that includes the rotating ring-shaped electron beam or a separate component.

According to a preferred execution of the invention, the individual target elements are arranged on the carrier so they can be replaced. This makes it possible to replace the costly target elements with new ones after they have worn out, but the ring-shaped carrier can still continue to be used.

The carrier and/or the beam delivery tube are preferably made of a heat-conducting material, especially copper. This makes it possible to eliminate heat better from the target elements and in addition facilitates low-cost manufacturing of the carrier.

It is advantageous if the discrete focal areas are arranged in an angle with respect to the plane of the circular path of the electron beam. As a result of this, an electron beam rotating in a plane parallel to the ring-shaped target can now be deflected by a small deflection angle, whereas in other state-of-the-art units generally a 90° deflection angle is necessary in order to ensure the perpendicular striking of the electron beam on the target. In this case, it is especially advantageous if the focal areas have preferably an angle of 58° with respect to the circular path plane of the electron beam.

According to another further development of the invention, it is advantageous for the carrier and/or beam delivery tube to have at least one cooling channel. This makes it possible to have good water cooling with which the temperature gradients occurring in the annular structure can be kept at low levels.

In this case, it is advantageous for the carrier and/or beam delivery tube to have several separate cooling channels that can be impinged upon. Adequate cooling is then possible with large diameters in particular, thereby eliminating the expected thermal expansion of the structural components.

Another design of the invention foresees the kinetic energy of the electrons that make up the electron beam to be adjustable. As a result of this, it is possible to adjust the electron energy to the most varied measuring purposes. In this case, the kinetic energy of the electrons can be adjusted within a range of 80 keV and 1,000 keV. Thus, it is possible to use the computer tomograph according to the invention for many different applications in medical and technical fields. For technical measurement purposes, energy intensities between 150 keV and 1,000 keV are needed.

However, it can also be advantageous in technical applications involving the examination of highly absorbent objects if the kinetic energy of the electrons exceeds 1 MeV. In this case, it is advantageous if a generally reduced weakening of the radiation occurs with higher generation voltages.

If the electrons have such high energies, it is better for the target elements to be arranged as irradiation targets that emit the radiation beam in the flying direction of the striking electrons. The rotating electron beam is deflected here in such a way that the electrons strike mostly radially towards the center of the irradiation target. In this case, the deflecting angle of the electron beam is 90°.

According to another execution of the invention, a compensation body has been arranged in the beam direction after the irradiation targets in order to maintain homogeneous the intensity of the radiation beam over the field of view.

Another further development of the invention foresees the irradiation targets to have an angle of preferably 45° with respect to the circular path of the electron beam. In this case, the compensation bodies are preferably shaped like a trihedron with an intersection angle of preferably 45°. As a result of this, a tight arrangement of the irradiation target can be achieved, although it would still be possible to have enough space for placing one compensation body per irradiation target.

In accordance with another further development of the invention, it is advantageous if the X-ray source can be simultaneously interspersed by a second annular electron beam. If in this case the target has the shape of a double focusing ring, this enables one to foresee twice the number of discrete focal areas to perfect the scanning and as a result of this.

For operating the double focusing ring, it is advantageous for the computer tomograph to have two electron sources, which increases joint beam power, but also opens up more application possibilities. Likewise, it is also possible to assign a switch made from kicker magnets, for example, for generating a second electron beam.

However, it is also possible to feed the two electron beams into two axially displaced X-ray sources. In this case, two identical designs of the ring-shaped target, the guiding media for the electron beam and the deflecting media for the latter are present. Here, the two electron beams could also be generated either by a second electron beam source or a switch. Preferably, two detectors are axially arranged to one another in this case.

It is particularly advantageous if the electrons of the second electron beam have a different kinetic energy with respect to the first electron beam. As a result of this, it is possible to carry out a volume scan simultaneously with two different energies.

It is also advantageous if the computer tomograph includes an additional detector allocated to the second electron beam. This makes it possible for a dual-energy simultaneous scan to assess measured values quickly. However, one single detector can also measure the transmissions.

It is also advantageous if the electron beam(s) can be fed tangentially into the X-ray source. In this case, the electrons can be generated in an electron gun, for example, and fed tangentially into the evacuated ring structure via optoelectronic elements.

So that the electron beam that has been fed can be guided towards a circular path in the X-ray source, it is advantageous if the media that guide the beam are made of coils or deflecting magnets. It is also advantageous if the number of guiding media corresponds to the number of saw tooth elements. In this case, every tooth in the target is equipped with its own deflecting magnet. Depending on the number of deflecting magnets arranged in the X-ray source, they must bend the beam by a precise number of angular degrees. According to a preferred design, the target has 721 teeth and 721 deflecting magnets arranged in it, deflecting the beam in each case by 0.5°.

It is also advantageous if the media for guiding and deflecting the electron beam can be individually controlled in sequence. Here, the electron beam sequentially strikes precisely one dot on every focal area. As a result of this, various stopping times of the electron beam can also be carried out on different focal areas as well.

According to a particularly advantageous further development of the invention, the media for deflecting the electron beam are created by kicker devices placed in the media to guide the electron beam. These can be executed either magnetically or also electrostatically. As a result of this, both the guidance and deflection of the electron beam towards the target can be accomplished in each case by a joint element. If the media for guiding the electron beam are made of deflecting magnets, then a very compact design of the computer tomograph can be achieved.

It is also advantageous for the deflecting angle of the kicker device to have an angle of 32°. Needless to say, other deflecting angles are also possible, each one depending on the angle of the focal area with regard to the plane of the circular path of the electron beam. In this case, it is advantageous that a deflection of the electron beam by 90° is not needed, as it is with other state-of-the-art units.

An advantageous further development of the invention foresees the deflecting angle of the kicker devices to be adjustable, thus allowing several target elements to be joined together with one deflecting device as well. As a result of this, the number of kicker devices can be reduced, thereby simultaneously creating more space for building the focusing and deflection.

It is advantageous if an electron lens is allocated to the kicker device, in which case the electron beam is shaped after deflection towards the focal point in such a way that an optimal focal magnitude results from this.

Furthermore, it is advantageous for the focal areas to preferably have a lead angle of 12° with respect to the axis of the ring-shaped target. Therefore, the optical focal point can be held low as well. Depending on the design, however, other lead angles can also be favorable.

According to a further development of the invention, it is advantageous if the focal point of the electron beam can be adjusted on the discrete focal areas. The adjustment of the focal areas can be done both with kicker devices and optoelectronic elements. In order to keep target corrosion to a minimum, the focal point can in turn be adjusted in each case on the target by some focal widths, just as executions of the focal point as a line and/or spring focus are possible. In this case, additional electron beam deflection devices can be foreseen as well.

It is advantageous if the electron beam focal point is executed as a line focus. As a result of this, the thermal burden on the target can be distributed over a larger area, thus allowing short scanning times even with higher radiation intensity. For example, it is advantageous for the line focus to have dimensions of 1 mm*10 mm. Therefore, if the lead angle is 6°, one obtains a virtual focus of about 1 mm*1 mm.

In this case, the line focus can be continuously moved on the target, something that must be taken into account in image reconstruction. For example, the focal point can be blurred over a length of 20 mm in order to reduce the instantaneous thermal load on the targets.

Alternatively or additionally, the focal point of the electron beam can be executed as a spring focus, which can also be accomplished with optoelectronic elements. The development of a spring focus can also reduce the instantaneous thermal load on the targets. In addition, there is also the possibility here to obtain more independent projections as a result of this and, depending on design, the effect of additional detector lines is achieved, without the detector really needing to have more lines or definition to be increased.

It is advantageous to allocate exactly one line of the detector to the spring focus, in which case the focus jumps in several places of the line. In this case, the focus can also jump in two or even more places of the detector line.

According to another further development, it is advantageous if several lines of the detector are allocated to the focus. In this case, the focus can jump several places in several lines as described above, but can also be blurred in several detector lines over a certain length. As a result of this, the number of the independent projections can be increased during one rotation without needing more detector lines to accomplish this. At the same time, the times for one rotation (and therefore, for the entire scanning time) can be favorably shortened.

Since it is possible to increase the number of projection directions in one jumping or blurring of the focal point in several lines, one can reduce the number of the individual target elements, in which case it would still be possible to obtain an adequate number of projections with good definition. As a result of this, the revolution time can be shortened even more, making possible a revolution duration of 50 ms and less.

If the focal point has been executed as a spring focus—in which case data are written in two detector lines—then it is advantageous if another target having many individual target elements is foreseen, arranged in a displaced way by a quarter period space with respect to the first target. As a result of this, an equidistant dense scanning of the object to be examined can be achieved after a full 360° rotation of the electron beam, since the share of the scope represented by one radiation source is increased. Together with the projections of the opposing side, a continuous scanning is therefore achieved.

In order to increase image quality and to reduce noise caused by scattered radiation, it is advantageous to allocate a scattered-ray grid equipped with ring lamellae to the detector. In this case, the ring lamellae can be oriented parallel to one another or in an angle directed exactly towards the focus.

It is advantageous if the scattered-ray grid can have between the ring lamella electromechanically adjustable transversal lamellae in the direction of the revolution of the electron beam. As a result of this, and depending on the length of the momentary focus, the transversal lamellae can be optimally oriented. It would be favorable for the adjusting angle of the transversal lamellae to have an angle of +/−34°. In this case, the adjusting angle depends on the measuring field diameter, the distance of the target ring to the isocenter and the distance of the detector ring to the isocenter.

A particularly advantageous further development foresees the photon fluence to be adjustable. This can be done, for example, by changing the electron beam current, as already known. It is especially advantageous if the photon fluence can be individually adjusted for every focal area. This facilitates the optimal adaptation of the photon fluence to the corresponding measuring conditions. In this case, it is preferable to adjust the photon fluence by regulating the stopping time of the electron beam in the individual focal point. As a result of this, the computer tomograph can always be operated at maximum current and full power, since the fluence in the corresponding focal point is regulated merely by the stopping time.

It is particularly advantageous if the photon fluence can be individually measured in every focal area by an irradiation chamber. In this case, every focal area can be allocated to an own irradiation chamber or arranged in a joint irradiation chamber. This allows one to easily support the modulation of the photon and to record it with measuring technology.

According to an especially advantageous further development of the invention, the stopping time of the electron beam is adjustable depending on a delivered dose of the detector elements allocated to the corresponding focal point. The electron beam will only continue to keep moving if the required number of photons has been recorded in the detectors. As a result of this, the fluence can in each case be optimally adjusted when the focal point is stationary according to different criteria.

It is furthermore advantageous if in the measuring field a region of interest can be pre-determined for which the measuring conditions, especially photon fluence, can be optimally adjustable. In this case, photon fluence is determined by the delivered doses allocated to the detectors found in the region of interest.

It is advantageous if the distance of the focal point to an isocenter is up to 100 cm, thus making possible more extensive medical applications. It is particularly advantageous if the distance of the focal point to the isocenter can be adapted to the dimensions of the object to be measured. The distance can be 130 mm to 1,000 mm, for example, thus making an optimal testing of the most varied objects to be measured possible. Since there are no more rotating parts in the computer tomograph according to the invention, the distance can be easily laid out according to the demands of the object to be measured. As a result of this, the computer tomograph can be adapted to the most varied technical and medical measuring purposes.

It is advantageous for the ring-shaped detector to be axially displaceable with respect to the ring-shaped target. In order to place the detector optimally with respect to the beam path, it can also be arranged in a slight inclination to ensure an almost perpendicular striking of the X-rays.

To prevent lower image quality caused by scattered rays, it is better to foresee an internal shield located between detector and target in the unit.

It is also advantageous if at least one fixed aperture ring is allocated to the ring-shaped target. In addition, it is also advantageous if an aperture adjustable in three planes is allocated to the ring-shaped target. As a result of this, the beam can be laterally restricted in an optimal way.

Furthermore, it is advantageous for the computer tomograph components to be arranged in a torsion-resistant supporting frame. As a result of this, various inclinations and even a horizontal operation with sitting patients is possible.

So the computer tomograph can be tilted in various positions, it has been advantageously placed on a stand that can be rotated, thus facilitating in each case the optimal representation of the object to be scanned. Preferably, a device for rotating the computer tomograph (for example, a motor operator) is foreseen in the stand.

Preferably, the computer tomograph can be rotated around a horizontal rotation axis parallel to the ring-shaped target. It is better for the rotating axis to run through the isocenter of the beam cluster. As a result of this, it is possible to achieve the tilting angle one is accustomed to.

Owing to the torsion-proof supporting ring structure, the computer tomograph can be operated in any desired position within the room. Therefore, it is advantageous if a device is allocated to the computer tomograph with which it can be moved freely in the room. This device can have the shape of a crane or robotic arm, for example. As a result of this, the entire computer tomograph can be freely turned and positioned in the room.

It is also advantageous if the positioning of the device in the room is controlled by a computer, thus allowing the computer tomograph to be positioned exactly with respect to the object to be measured. This facilitates examinations and treatments controlled under X-rays. Its use in surgery is also possible. A computer controls the positioning of the computer tomograph on the operating table and tilts it in such a way that the body region in question can be ideally shown. At the same time, the tilting allows optimal access to the operating site.

The computer tomograph according to the invention can advantageously be connected to another unit, such as a TomoTherapy apparatus or to imaging systems such as a PET. If the unit also has a ring structure, then both of them can be joined together to form one single unit.

In this case, it is advantageous if a computer tomography can be carried out during a radiation therapy session. Thus, a computer tomography data capture of the targeted volume can be done during certain time periods or continuously while radiation therapy takes place. Thanks to X-ray checking, radiation therapy can be optimally carried out, since the unit parameters of the radiation therapy unit can be subsequently adjusted. Likewise, a subsequent guidance of movements of the targeted volume is also possible.

In such a combined unit, it is particularly advantageous if a radiation therapy unit can be arranged in such a way that it can be axially displaced between the ring-shaped target computer tomograph.

The corresponding inclination or lead angle of the focal areas of the computer tomograph allows one to take pictures exactly from the isocenter of the combined unit or irradiated region, thus making it possible to optimally control the radiation therapy to be performed, In this case, the inclination of the detector ring is adapted to the angle of the central beam of the beam bundle, thus ensuring a perpendicular striking of the beams on the detector elements.

In technical application fields, the computer-controlled positioning of the computer tomograph allows, for example, a robotic arm to perform the automated measuring process in various room directions.

Especially if the computer tomograph should not only be used in stationary operation, it is advantageous to also foresee (apart from the adjusting possibilities typical of initial assembly) to have easily adjustment options for the X-ray source, the target and the detector to one another and/or with respect to the isocenter.

Furthermore, it is advantageous if the computer tomograph could also be used as a mobile unit. As a result of this, and especially in the case of technical applications, a checking of components would be possible in situ, something that would be particularly useful in large technical installations. For mobile use, only the corresponding voltage supply would be needed.

BRIEF DESCRIPTION OF THE DRAWINGS

Additional advantages of the invention are explained with the help of the following examples. They show.

DETAILED DESCRIPTION

Figure 1:
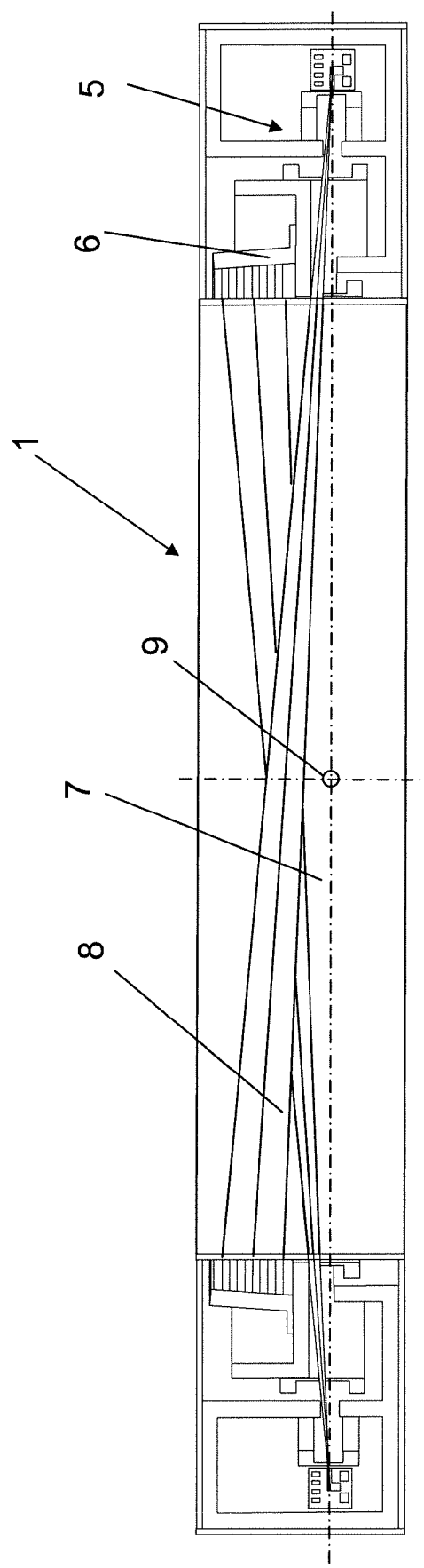
FIG. 1 a diagrammatic cross-sectional view of a computer tomograph according to the invention, FIG. 2 a cross-sectional view through the ring-shaped X-ray source and the allocated, ring-shaped detector, FIG. 3 a diagrammatic view of a ring-shaped target with saw tooth elements seen from the top and side, FIG. 4 a diagrammatic view of a target built as double focusing ring with media for guiding and deflecting the electron beam, FIG. 5 a diagrammatic cross-sectional view of a beam delivery tube with cooling channels and a double focusing ring, FIG. 6 a diagrammatic cross-sectional view of a computer tomograph according to the invention with two axially displaced X-ray sources, FIG. 7 a top view of the target elements and the deflection devices of another computer tomograph according to the invention for medical applications, FIG. 8 a diagrammatic view of the ring-shaped structure of a computer tomograph according to the invention for technical applications, FIG. 9 a diagrammatic view of the arrangement of the irradiation target of a computer tomograph for technical applications, and FIG. 10 a diagrammatic view of the arrangement of the irradiation targets and compensation bodies.

Reference will now be made to embodiments of the invention, one or more examples of which are shown in the drawings. Each embodiment is provided by way of explanation of the invention, and not as a limitation of the invention. For example features illustrated or described as part of one embodiment can be combined with another embodiment to yield still another embodiment. It is intended that the present invention include these and other modifications and variations to the embodiments described herein.

FIG. 1 shows a diagrammatic cross-sectional view of a computer tomograph 1 according to the invention through the symmetrical axis of the structure. The computer tomograph 1 consists of a ring-shaped structure in which the most important parts of computer tomograph (such as the X-ray source 5 and a ring-shaped detector 6) are arranged. In this case, the ring-shaped structure encloses a measuring field 7 that can be irradiated by an X-ray beam cluster 8 that turns concentrically around itself. In the center of the ring structure is the isocenter 9 of the arrangement in which the object to be measured (not shown here) can be placed. Finally, the X-rays strike a detector 6 placed in front of it and consisting, as is known, of many detector elements placed in rows. The detector 6, the X-ray source 5, and the electron source (not shown here) for generating an electron beam are in this case stationary executed, so that the computer tomograph 1 has no movable components.

Figure 2:
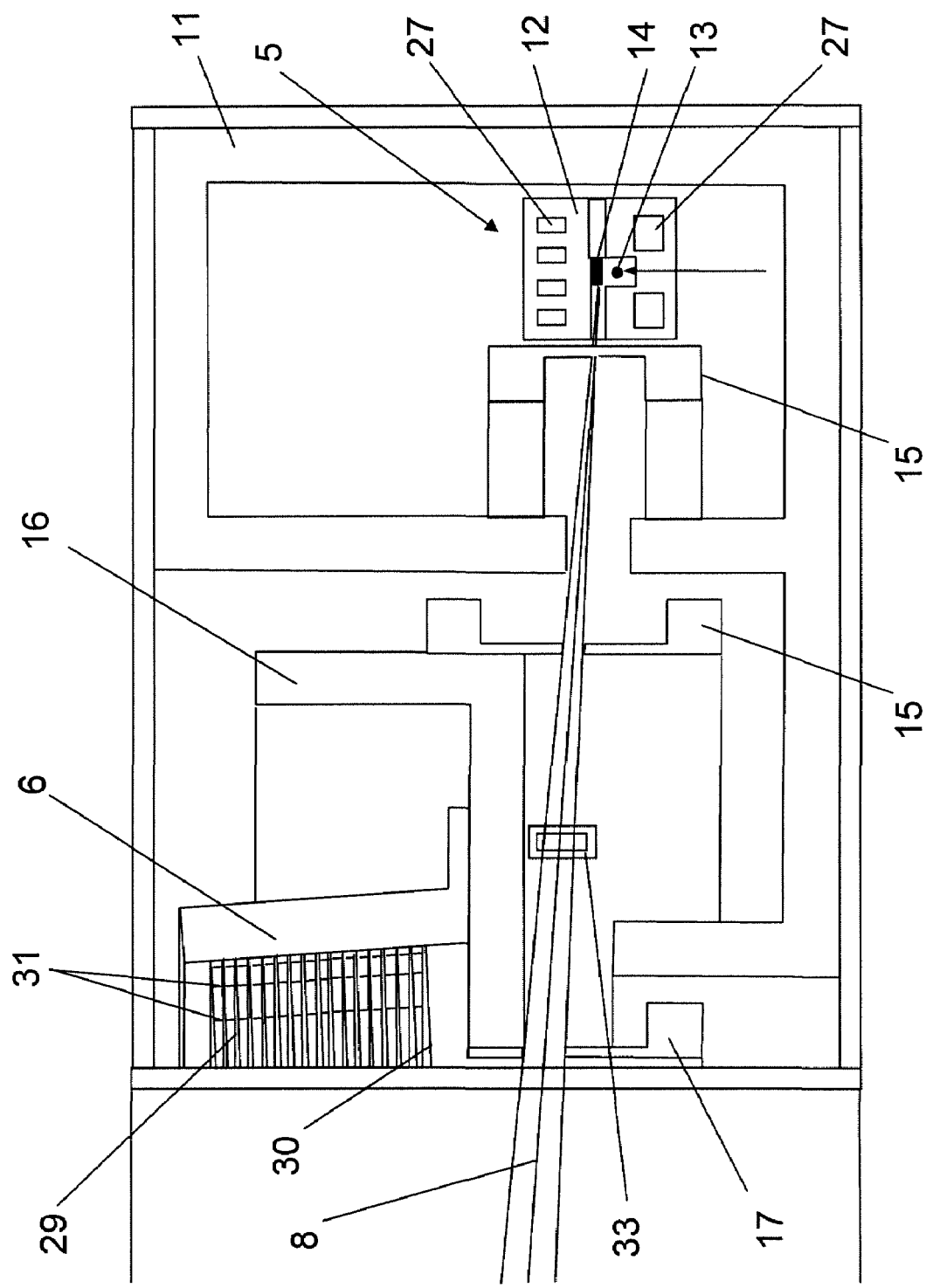

FIG. 2 shows a detailed diagrammatic view of the cross-section near the X-ray source 5 and the detector 6. The computer tomograph 1 has a ring-shaped, torsion-proof supporting frame 11 on which the computer tomograph components are arranged. On the supporting frame 11, a beam delivery tube 12 has been arranged, in which an electron beam 13 rotates around a circular path. The electron beam 13 is kept on a circular path by media guiding it (see FIG. 4). Furthermore, a largely ring-shaped target 14 has been arranged on the beam delivery tube 12, and it is known that the striking of the deflected electron beam 13 on the target generates the X-rays. The target has been placed on the outer wall of the beam delivery tube 12. For the best possible beam guidance, the generated X-ray cluster 8 is formed several times by apertures that can be executed either as fixed-aperture rings 15 or as adjustable apertures 17. Axially displaced to the ring-shaped beam delivery tube 12 with the target 14, a fixed detector 6, likewise executed with a ring shape, has been arranged. To prevent erroneous evaluations caused by scattered radiation, a shield 16 located inside the unit has been arranged between the detector ring 6 and the target 14.

The detector 6 is placed slightly inclined in accordance with the inclination of the central beam of the beam cluster in order to ensure the perpendicular striking of the X-rays as much as possible.

According to another execution of the invention not shown here, the computer tomography unit can be combined with a radiation therapy unit. In this case, the gantry of the radiation therapy unit is arranged between the ring-shaped target 14 and the detector ring 6. The corresponding inclination of the focal areas allows one to orient the beam cluster exactly on the region to be treated; in this case, the inclination of the detector 6 must be adjusted to the path of the central beam. This allows an optimal radiological control of the treatment.

Figure 3:
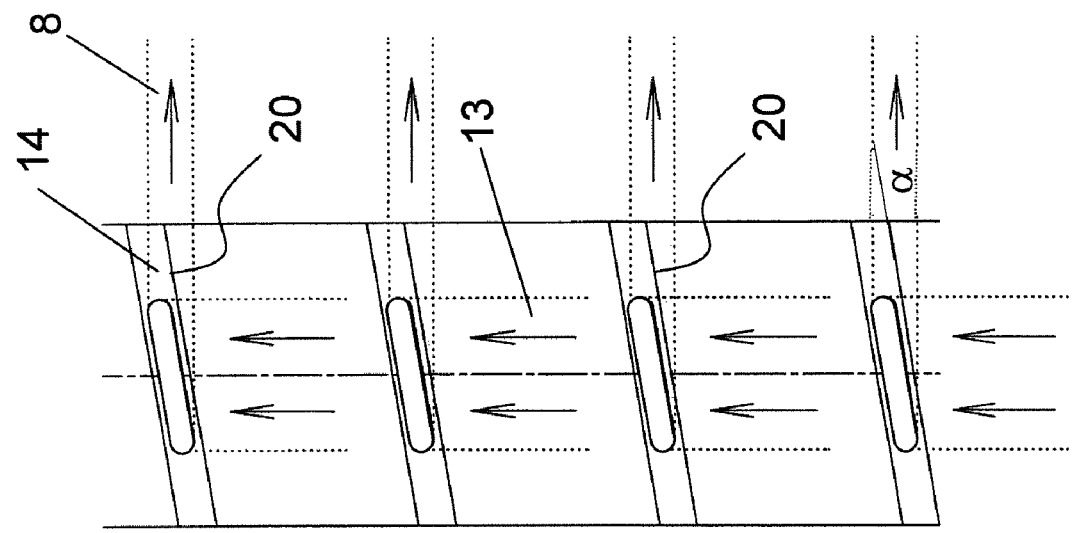
Figure 3:
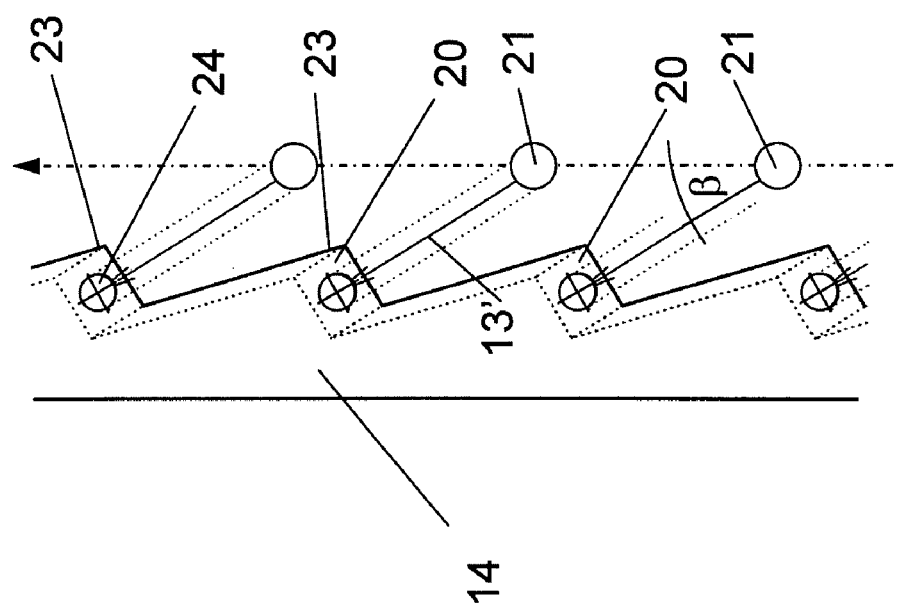

The invention foresees the largely ring-shaped target 14 to have numerous discrete focal areas 20 (FIG. 3). In the beam delivery tube (not shown here), an electron beam 13 rotates in a circular path parallel and concentrically to the ring-shaped target 14. The electron beam 13 is kept on the circular path by media that guide the electron beam. The electron beam deflection media 21 guide the electron beam 13 to the corresponding focal areas 20. Thus, the scanning of the target 14 by the electron beam 13' does not take place in a continuously rotating way, but discontinuously along precisely fixed points. As a result of this, it is possible to improve image quality with respect to state-of-the-art units, since the radiation detected in detector 6 can in each case be exactly allocated on a precise spot in the focal area 20. The focal areas 20 are preferably arranged in an angle with respect to the circular path plane, 58° in the figure shown here. As a result of this, the ring-shaped rotating electron beam 13 can in each case be merely deflected by the deflecting angle β, here 32°. The generated X-ray cluster 8 is emitted here in largely perpendicular fashion with respect to the incoming electron beam 13', as can be recognized in the lateral view (right image) of FIG. 3. The angle β of the focal areas allows the advantageous reduction of the cross-section of the emitted X-ray cluster 8.

As can be recognized in the lateral view of FIG. 3, the focal areas 20 also have a lead angle α with respect to the axis of the ring-shaped target. In the illustration shown here, the lead angle α is 12°, thus allowing the cross-section of the emitted cluster to be reduced by about ⅕, as can be seen in the drawing.

As can be recognized in the top view (left illustration) of FIG. 3, the target 14 has a stepped ring-shaped structure with saw tooth elements 23. In this case, the division of the saw tooth elements 23 corresponds here to at least a 2°-division of the entire circle. Compared to the current state of technology, a row of many fixed images is obtained here instead of a continuously running image, which allows the quality of reconstruction to be improved upon. At the same time, this also makes it possible to reduce radiation exposure in the patient.

The target 14 consists preferably of a tungsten alloy, but it is also possible to have just sufficiently large, thin tungsten layers creating many target elements and to arrange them on a saw tooth element 23 of a stepped ring-shaped carrier. The carrier can be mounted on the beam delivery tube 12 or be executed as one piece with it. The individual target elements can be arranged on the carrier so they can be replaced after having worn out, while the carrier can keep being used. The carrier could also have holding devices for the target elements, which would also have a pin aperture as lateral shields. The replacement of the target elements can be done very easily in this case, thereby greatly reducing costs, since the expensive tungsten is not used up as quickly.

It is better for the target 14 to have 361 or 721 steps, and a better definition of the obtained images can be expected with more steps. As can be seen in FIG. 3 or in the following FIG. 4, a medium 21 for deflecting the electron beam is foreseen for every saw tooth element 23. The carrier of the target 14 can preferably be made from an economical copper material, which also provides good heat conduction out of the region of the target 14.

Figure 4:
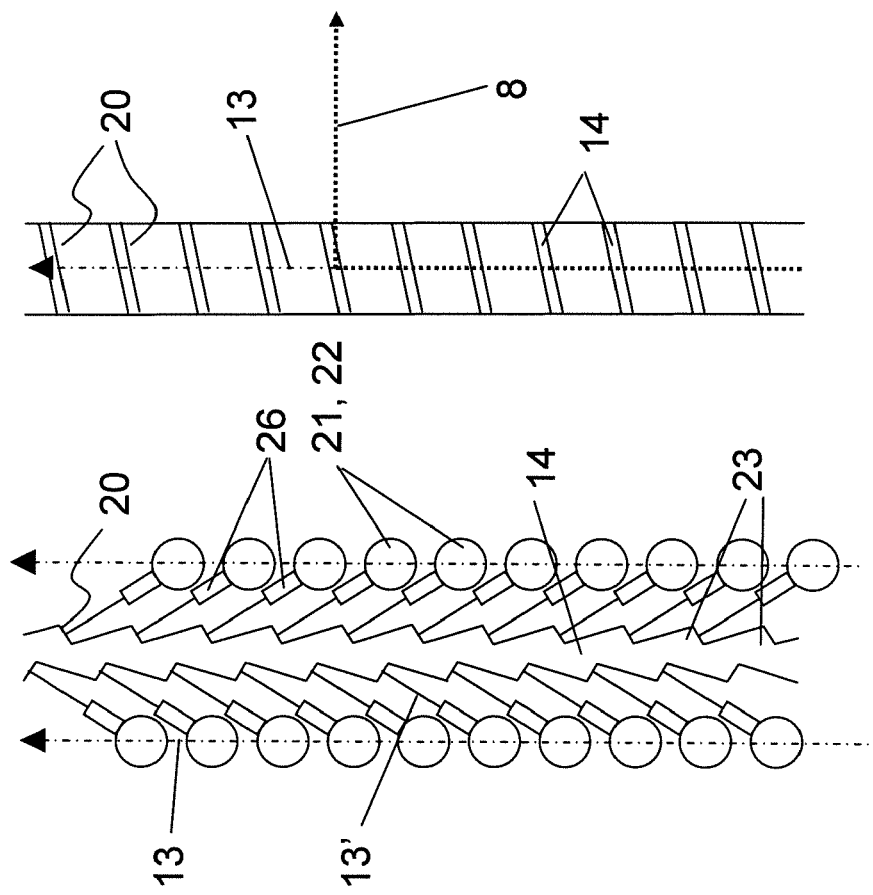

To keep corrosion of the targets 14 to a minimum, it is better to let the focal point 24 wander by a few focal widths on the focal area 20. This can be accomplished by the targeted control of the deflecting media 21. Preferably, an electron lens 26 should be allocated to the deflecting media 21, as can be seen in FIG. 4. As a result of this, the burning off of the target material can be reduced, thereby prolonging useful life.

As can be seen in FIG. 2, the beam delivery tube 12 has cooling channels 27 through which a coolant can flow, preferably water. This allows heat to be very effectively transported out of the region of the target 14. The rotating water cooling system can at the same time keep the temperature gradient on the radius very low. Especially with larger diameters it can also be advantageous if the cooling channels 27 can be separately impinged.

Figure 5:
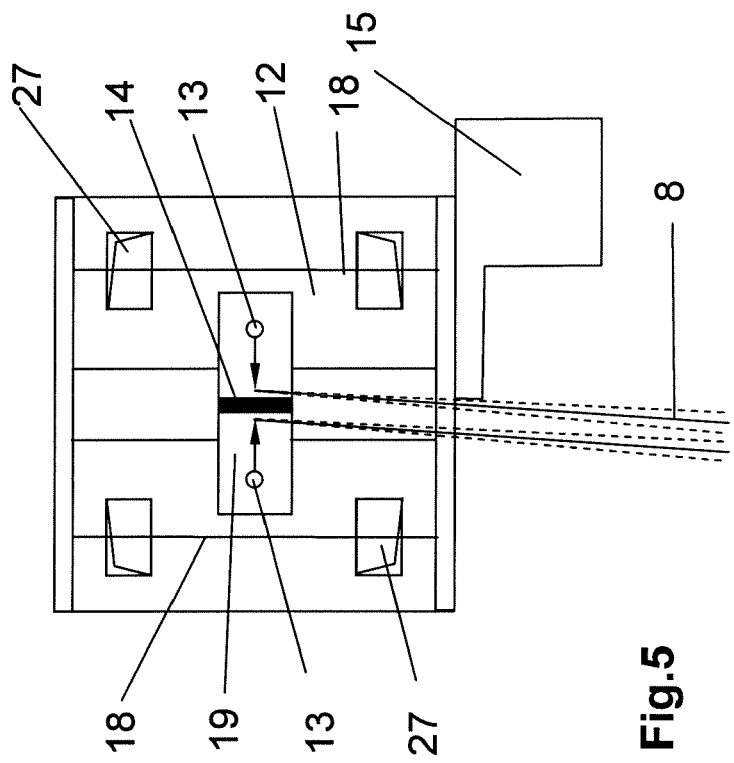

FIG. 5 also shows a beam delivery tube 12 with cooling channels 27. The beam delivery tube is in this case composed of several disk-shaped ring elements, in which the cooling channels 27 have been inserted as grooves. Here, the dividing line 18 has been placed near the neutral fiber to prevent problems caused by draft. A cavity 19, in which the electron beam 13 rotates in a vacuum and the target 14 is arranged, is created between the ring elements composed in pairs.

The execution of the ring-shaped target 14 as a double focal ring is shown in FIG. 4. In this case, the target 14 can be made of tungsten lamella or only of tungsten (as described under FIG. 3), but it has a stepped annular structure with saw tooth elements 23 on both sides. If the target 14 is executed as a double focal ring, then the definition of the generated images can be greatly improved with simple measures. In this case, the beam delivery tube 12 is interspersed with two ring-shaped electron beams, as can be seen in FIG. 5. The electron beams 13 run parallel to each other around a circular path and are axially displaced with respect to the target ring 14. FIG. 4 also shows the target 14 and the deflection of the electron beam 13 as well as the generation of the X-ray cluster 8, in each case in a top view (left illustration) and a lateral view (right illustration). The electron beams 13 are guided by media 22 for guiding the electron beam along the circular path. In this case, the guiding media 22 for the electron beam 13 can be made of coils or preferably of deflecting magnets. Preferably, the number of deflecting magnets should be the same as the number of saw tooth elements 23, but a different number of deflecting magnets can be available. The electrons could also be guided by coils, but this design would need more space.

In the illustration shown, the guiding media 22 for the electron beam 13 along the circular path have also been executed as deflecting media 21 for the electron beam 13. In order to accomplish this, the deflecting magnets have in each case a kicker device that can be magnetically or electrostatically executed. Every kicker device deflects the electron beam 13 to the discrete focal areas 20. Preferably, the kicker device should be allocated to an electron lens 26, which shapes the deflected electron beam 13' according to the desired focal size. This makes it possible, especially with the angles of the focal areas 20, to achieve an advantageous small focal point 24, which—when seen from the isocenter—measures only 1 mm in both dimensions.

A switch can be allocated to the electron source to generate the second electron beam 13. The switch can (as already known) be made of deflecting magnets with a kicker device, but the computer tomograph 1 can also include two electron sources.

The electron source not shown here is made preferably in the shape of an electron gun and tangentially feeds the electron beam 13 with optoelectronic elements. In this design, the electron gun is placed outside the X-ray source and can therefore be executed in any way. Thus, the mounting of a second electron gun is possible without any problems. In this case, the electron gun can be executed as a thermal cathode or as an electron accelerator. For medical applications, the electrons have kinetic energies of approx. 80 to 150 keV. However, larger and smaller structural components can also be examined with kinetic energies reaching up to 1,000 keV, and for certain technical applications energies exceeding 1 MeV can be foreseen. In these cases, a linear accelerator or microtron accelerator can be the electron source.

Figure 6:
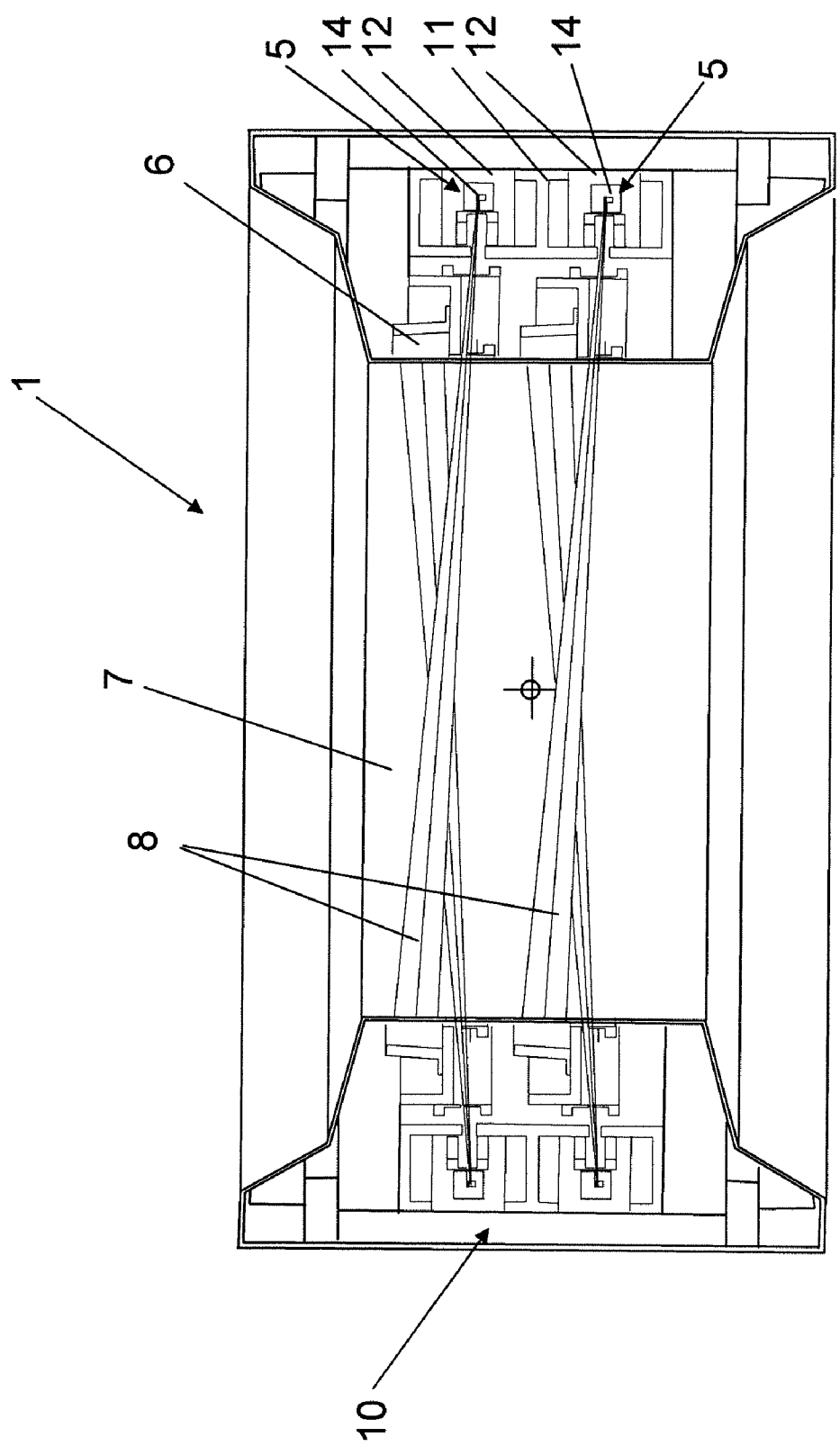

It is also possible to arrange two axially displaced X-ray sources 5 in the computer tomograph 1. FIG. 6 shows a horizontal cross-sectional view of a computer tomograph 1 according to the invention. In the illustration shown, there are two axially displaced X-ray sources 5 with beam delivery tubes 12, two ring-shaped targets 14, as well as the corresponding media for guiding 22 and deflecting 21 the electron beam 13 towards the in target 14. Two detectors 6 have also been arranged by axially displacing them.

Such an arrangement offers especially the possibility of adjusting the second X-ray source 5 to a second energy. As a result of this, a volume scan can be simultaneously measured with two energies (dual energy). Since in each case a detector 6 has been allocated to an X-ray source 5, very fast data processing is possible. However, it is also possible to measure the transmissions of both X-ray sources 5 in a single detector 6, which is a more economical solution. To operate the computer tomograph 1 with two different energies, it is better to allocate two electron sources to the computer tomograph, especially electron guns. The target 14 is adjusted to the different energies in the same way.

As can be seen in FIG. 2, a scattered-ray grid 29 with annular lamella 30 has been allocated to the detector 6. This makes it possible to reduce noise, thereby greatly enhancing image quality. The annular lamella 30 can be easily arranged parallel to one another. In a preferred design, every individual annular lamella 30 is exactly oriented in a specific angle towards the focal point 24 in the opposing target 14. In this design, it is especially advantageous if the scattered-ray grid 29 has electromechanically adjustable transversal lamella 31 located between the annular lamella 30 in the rotational direction of the electron beam 13. The scattered-ray grid 29 has in this case the shape of a rectangular grid. The transversal lamella 31 can as a result of this also be exactly oriented toward the beam focus. The electromechanical guidance can be carried out with piezo technology, for example.

The adjustable transversal lamella 31 make it possible to optimally guide the X-rays to the detector 6. The adjusting angle of the transversal lamella depends in this case on the diameter of the measuring field. A further development of the invention might foresee the adjustable transversal lamella 31 to be moved by +/−90° in order to close them fully. As a result of this, individual detector elements of the detector 6 could be protected from excessive photon fluence; especially those detectors lying outside the measuring cone are rendered mute.

With the computer tomograph 1 according to the invention equipped with numerous discrete focal areas 20 it is also possible to individually adjust the photon fluence for every focal area 20. Depending on the angle and absorption, this makes it possible to modulate photon fluence. In conventional computer tomograph units, the modulation of photon fluence is done by modulating the tube current. Thanks to the fact that the target 14 has been made discrete according to the invention and to the discontinuous scanning, it is possible with the computer tomograph 1 according to the invention to adjust the photon fluence just by regulating the stopping time of the electron beam 13 in the individual focal point 24. In this case, the computer tomograph 1 can always be operated with full power at maximum current.

The stopping time of the electron beam is preferably regulated by measuring the photon fluence in the corresponding focal point 24. It is also possible to regulate stopping time depending on a delivered dose of the detector elements allocated to the corresponding focal point 24. In this case, the electron beam 13 will only keep traveling if a sufficient dose has been delivered.

To measure photon fluence, as shown in FIG. 2, an irradiation chamber 33 has been arranged outside the X-ray source 5. Instead of numerous single chambers 33 per focal area 20, it is also possible only to use only one large ring-shaped chamber. Since in each case only one focal point 24 emits X-rays 8 at the same time, the signal for the measurement can always be exactly allocated to a focal area 20 if the time constant has been correspondingly chosen. The modulation of the photon fluence depending on delivered dose on the detector 6 and the corresponding charge in the individual focal area 24 make it possible to optimally adjust the radiation dose to the object being measured and therefore to considerably reduce radiation exposure in patients.

The computer tomograph 1 according to the invention can therefore be adapted both to the object being measured and to the most varied measuring tasks in technical and medical fields. Since there is not a single moving part in the computer tomograph 1, it can be used in many applications. Since the electrons can be generated in an X-ray source 5 arranged externally as electron source instead of in a conventional X-ray tube, electron beams 13 with the most varied kinetic energies can be generated. Therefore, electrons having kinetic energies ranging from 150 keV to 1,000 keV can be made available for technical measuring purposes.

It is also possible to variously adjust the photon fluence in the individual focal areas 20 and optimally for every measuring condition. Thus, a region of interest can be pre-determined in the measuring field 7, for example, and the photon fluence for measuring conditions can be optimally adjusted in this same region of interest. As a result of this, the quantum noise and the effect of too-low transmission (starvation) can be especially reduced after strongly absorbing structures. In this case, the doses delivered by the detectors 6 determine the fluences.

It is also possible with this computer tomograph 1 according to the invention to adjust the distance of the focal point 24 to the isocenter 9 to the corresponding dimensions of the object being measured. The distance in this case can be in the range from 130 mm to several meters. As a result of this, both compact structural components as well as long and thin components can be optimally tested, especially in technical applications. Since the computer tomograph 1 according to the invention consists merely of a slender ring-shaped structure, it is easily possible to test measuring objects in a continuous operation.

The local definition of the reconstructed "image" of the weakening values of the object depends on a whole range of factors, one of them being the scanning rate per rotation. A 180°-scanning is sufficient for this, since in principle a scanning in opposite direction contains the same physical information. In case of the scanning made discrete (in approximately 1°-increments, for example), one obtains therefore 180 projections of the object that can be used for "image reconstruction". A clever arrangement of the target ring, however, can also increase the number of independent projections.

The preferred target structure of the invention utilizes an odd number of target areas per 360° rotation (361 or 721, for example). This arrangement according to the invention allows both a "faster" scan over 180° with approx. 180 or 360 projections (fewer dose per patient, lower local definition, shorter calculation time, somewhat more blurred result) and a "slower" scan with one-half pitch with about twice the number of projections, in other words 361 or 721. To the patient, this means about twice the dose, longer calculation time, but also a sharper result and a largely artifact-free reconstruction.

It is also within the scope of the invention to turn the entire ring structure 2 in small increments in the region of target's angle distance (by 1°, for example) in order to basically increase scanning per rotation as desired. As a result of this, a considerably higher definition can nonetheless be accomplished with a 361-step target in one rotation. This design can be advantageous if material testing has very high requirements.

The slender design of the ring structure without moving structural components can also enhance medical applications. For example, the distance of the focal point 24 to the isocenter 9 can be up to 100 cm in medical applications. It is also possible to place the entire computer tomograph 1 in various working positions with suitable means. It is not required to fix it in one standing position. Thus, it is also conceivable to examine sitting patients. Since in this case the components of the computer tomograph 1 have been arranged in a torsion-proof supporting ring structure, no losses in image quality should be feared. It is also possible to operate under X-ray control with the computer tomograph 1 according to the invention.

FIG. 7 shows a top view of the target elements and of the deflecting devices 21 of another computer tomograph 1 used for medical applications. The illustration shows a top view (left) of FIG. 3. In contrast with the illustration of FIG. 3, an additional target 14' has been foreseen here, consisting of individual target elements, as described. This target also consists of numerous individual target elements with discrete focal areas 20. Here, the individual target elements of a target have been arranged in each case at a certain distance from one another along a circular path. The additional target 14' has been arranged in such a way that the individual target elements have been displaced by one quarter period distance a/4 with respect to the first target elements.

Such an execution is advantageous if two lines of the detector 6 (not shown here) have been allocated to the focal point of the electron beam 13, here indicated with a dash and dot line. If the focal point data are written out in two lines, then one already obtains twice the number of independent projections.

If in addition to the first target 14 another target 14' is arranged displaced by a quarter period and a second detector line is allocated to this second target 14', then the full circle can be entirely filled with beam sources as a result of this, as explained below in more detail.

The individual target elements have been here, as shown in the illustration of FIG. 3, arranged in such a way with respect to the rotating electron beam 13, that a deflecting angle β of 32° results from this. Additionally, the individual target elements have a lead angle α of 6° here. With a correspondingly executed line focus (not recognizable in this view), a more favorable virtual focal point can be achieved with a lead angle of 6°.

Preferably, an odd number of target elements should be distributed along the perimeter of the full circle, so that the gaps I between the individual target elements are in each case struck by a beam from the opposite side of the target ring. As already described, additional independent projections are obtained through the beams of the opposite side of the ring. If in addition to the first target 14, another target 14' is arranged in a displaced way, then both target elements are in each case sequentially scanned by the corresponding deflected electron beam 13'. The gap L, which as a result of this is initially created on the perimeter of the full circle, and from which at first no information is obtained, is finally filled during one rotation of the electron beam by the radiation of the target elements located on the opposite side. As a result of this, an equidistant dense scanning of the object can be achieved after the electron beam has completed one 360° rotation, whereby in contrast to the arrangement of only one target 14 (as described in FIG. 3) twice the number of projections is obtained in this case.

Depending on the geometric execution of the individual target elements and the selection of the defecting angle β, a full covering of all angle regions of the full circle can be achieved as a result of this, thereby making continuous scanning possible. However, even if no continuous scanning can be accomplished, the equidistant scanning of the object by the beams of the opposite side of the ring is very advantageous to prevent artifacts through the gaps I between the individual target elements.

At the same time, the arrangement of an additional target 14' can reduce the instantaneous thermal load. The arrangement of an additional target 14', arranged in a displaced way by one quarter period with respect to the first one, also allows one to reduce the individual target elements on the target 14, 14'. The distance a between the periodically successive target elements becomes larger as a result of this, so that more structural space becomes available for the deflecting elements 21 and the electron optics. This arrangement also makes it possible to arrange an additional ring with pin apertures, which also collimates the generated X-ray on the ring plane.

At a certain spring focus frequency, with which the focus jumps back and forth among the individual lines, significantly shortened scanning times are hereby achieved. Rotational times of 50 ms and less can be obtained. In addition, with the corresponding arrangement of the individual target elements on different targets 14, 14' an oversampling is possible as well (in other words, a double covering of the full circle). Apart from the shortened duration of the scanning, the three dimensional definition (in other words, the definition in all three axis) can be improved with the design described herein. At the same time, the dose delivered to the patient can be reduced, since more information is obtained with one rotation.

Figure 8:
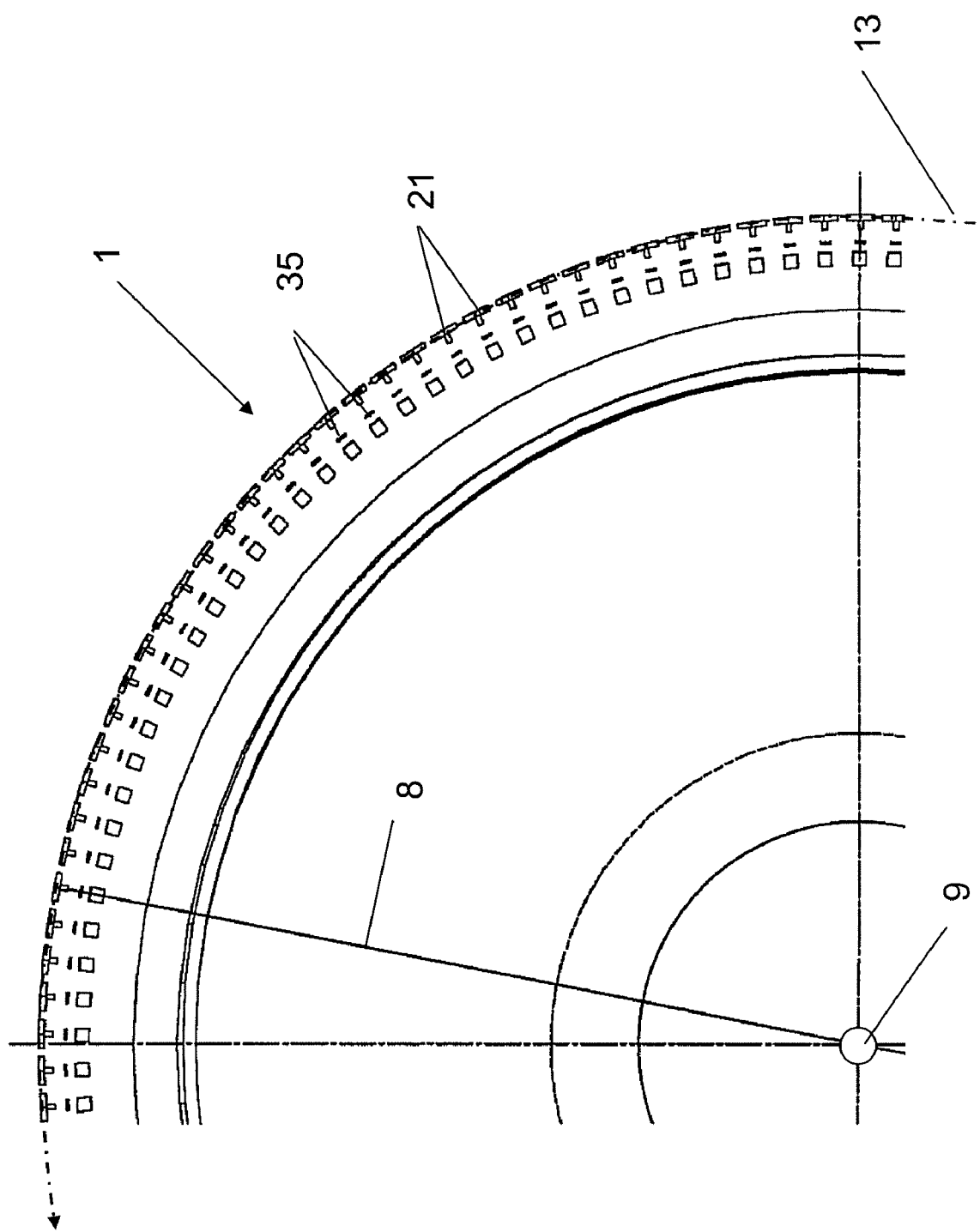

FIG. 8 shows a diagrammatic illustration of a computer tomograph 1 according to the invention for technical applications, where the view shows the ring-shaped structure of the computer tomograph 1. The illustration shows the annular structure of the computer tomograph 1, in which case the individual target elements have been executed as irradiation targets 35. For the materials testing of larger, heavier or strongly absorbing objects, kinetic energies of a magnitude between 1 and 3 megaelectron volts are desired, as opposed to medical applications. These magnitudes can be generated with the suitable accelerator (designed as a linear or microton accelerator) in an external electron gun and fed tangentially, for example, into the beam delivery tube as described.

Since with such high energies the maximum radiation beam occurs in the traveling direction of the striking electrons, the irradiation targets 35 are in this case arrange din such a way that the generated X-rays 8 is emitted towards the isocenter 9 of the computer tomograph 1. Here, the electron beam 13 does not travel parallel to the target ring, but along a circular path having a larger radius than the target ring. The deflecting devices are arranged in such a way here that the electron beam 13 is deflected in each case by 90° before the target so the electrons fall as radially as possible towards the center die. Contrary to the executions described above, only one point focus is generated here.

Two compensating bodies 36 have been mounted in beam direction after the irradiation target 35, and these bodies can be made of stainless steel, for example. They serve to maintain the X-ray intensity over the field of view as homogeneous as possible. To keep the size of the compensating body 36 small and to accommodate it without overlapping, they are mounted compactly on a ring (not shown here) behind the irradiation targets 35, whereby the ring has a kind of sawtooth structure.

According to another design (not shown here), it can also be advantageous to combine several irradiation targets 35 (such as three targets) with a deflecting device 21. In this case, the electron beam 13' is interchangeably guided from the pure 90° deflection towards the other targets as well. As a result of this, the number of deflecting devices 21 or kicker devices can be reduced, thus resulting in more space for building the deflection and focusing.

For operating with such high energies, the detectors 6 must be correspondingly adapted, in which case solid-state detectors are preferentially used. The other structural elements have not been shown here and generally correspond to the ones with lesser energy already described for medical applications. However, an improved shielding against scattered radiation is needed, and for this purpose a scattered-ray grid 29 can be arranged (as described in FIG. 2), made preferentially from rigid metal rings such as tungsten, for example. The shielding of the entire structure against transmission radiation must be correspondingly executed in the same way. Furthermore, the apertures must be adapted to the higher penetration of the hard radiation, so it is recommended that tungsten apertures be used.

In this case, the dimensions of the computer tomograph 1 can also be adapted to the examination of very large objects. Thus, the diameter of the ring-shaped target 14 can measure up to 8 m, in which case 601 individual target elements are arranged on the perimeter. Here, there is the possibility to execute the ring-shaped target 14 in the shape of a polygon made up of individual, straight partial segments, since they are easier to manufacture especially in the dimensions mentioned here. Therefore, in this case, a certain number of individual target elements are arranged on a straight partial segment. Finally, the individual partial segments are joined vacuum-tight to one another.

FIG. 9 shows a diagrammatic representation of the arrangement of the irradiation targets 35 of a computer tomograph 1 for technical applications. As described under FIG. 8, the individual target elements have been executed as irradiation targets 35 for technical applications using high electron energies. In this case, as already described, the electron beam 13 travels along a circular path that has a larger radius than the irradiation target 35 and is deflected from there in each case by 90° towards the isocenter 9 of the device. The dots on the irradiation target 35 indicate this.

A dense scanning (i.e. projections from every angle region of the full circle if possible) is desired if the computer tomograph 1 is designed for high energies. Since in each case an additional compensating body 36 that must lie on a smaller radius must be arranged, there can be space problems for the compensating bodies 36 with the compact arrangement of the irradiation targets. Therefore, in this case the individual irradiation targets 35 have been obliquely arranged in an angle of 45° with respect to the electron beam 13.

The compensating bodies 36, not visible in this illustration, have the shape of a trihedron here and are also arranged in an angle of 45° with respect to the rotating electron beam 13. The trihedral design allows the compensating bodies 36 to be arranged in spite of the densely placed irradiation targets 35. In this case, a cross-section of the trihedron having a lead angle of 45° becomes effective as a compensating body. FIG. 10 shows a cross-sectional view of the arrangement of the compensating bodies 36 with respect to the irradiation target 35; a view of towards arrow R of FIG. 9 is shown.

Additionally, the irradiation target 35 can be transversely scanned at an angle of 45°, as indicated by line 35. In addition to the deflecting devices 21, this design includes more scanning magnets (not shown here) located between the rotating electron beam 13 and the irradiation target 35. The definition of the generated image can be enhanced as a result of this arrangement.

According to another variant, the focal point can also be designed as a spring focus here, in which case the data are written out in two or even several detector lines. The paths of the spring focus are indicated by the lines 39 in FIG. 9.

Thus, it is also possible to almost completely scan the full circle with high-energy computer tomographs 1 and to optimize definition.

The invention is not restricted to the execution examples shown here. Variations and combinations within the scope of the patent claims fall under the invention as well.

The invention claimed is:

1. A computer tomography system, comprising:
   at least one stationary electron source configured for generation of an electron beam;
   a ring-shaped stationary X-ray source enclosing a measuring field, said X-ray source comprising a ring-shaped target and media arranged for coaxially guiding the electron beam along a circular path towards said target, and media arranged to deflect the electron beam towards the target for generation of an X-ray bundle that irradiates said measuring field from different directions;
   a stationary detector arranged in a ring shape and comprising a plurality of detector elements used for computer generation of an image being examined in said measuring field;

said ring-shaped target comprises a plurality of discrete focal areas arranged such that said plurality of focal areas are discontinuously scanned through respective focal points of the electron beam; and wherein said ring-shaped target comprises a stepped ring structure with an odd number of saw-toothed elements configured thereon, each said saw-toothed element including an irradiation target and a respective compensating body.

2. A computer tomography system, comprising:

at least one stationary electron source configured for generation of an electron beam;

a ring-shaped stationary X-ray source enclosing a measuring field, said X-ray source comprising a ring-shaped target and media arranged for coaxially guiding the electron beam along a circular path towards said target, and media arranged to deflect the electron beam towards the target for generation of an X-ray bundle that irradiates said measuring field from different directions;

a stationary detector arranged in a ring shape and comprising a plurality of detector elements used for computer generation of an image being examined in said measuring field;

said ring-shaped target comprises a plurality of discrete focal areas arranged such that said plurality of focal areas are discontinuously scanned through respective focal points of the electron beam;

wherein photon fluence is individually adjustable for each said focal area by regulating the stopping time of the electron beam at each said focal area; and further comprising an irradiation chamber configured for individually measuring photon fluence at each said focal area.

3. A computer tomography system, comprising:

at least one stationary electron source configured for generation of an electron beam;

a ring-shaped stationary X-ray source enclosing a measuring field, said X-ray source comprising a ring-shaped target and media arranged for coaxially guiding the electron beam along a circular path towards said target, and media arranged to deflect the electron beam towards the target for generation of an X-ray bundle that irradiates said measuring field from different directions;

a stationary detector arranged in a ring shape and comprising a plurality of detector elements used for computer generation of an image being examined in said measuring field;

said ring-shaped target comprises a plurality of discrete focal areas arranged such that said plurality of focal areas are discontinuously scanned through respective focal points of the electron beam; and wherein distance of said focal points to an isocenter of said measuring field is adapted to dimensions of the object measured in said measuring field.

4. A computer tomography system, comprising:

at least one stationary electron source configured for generation of an electron beam;

a ring-shaped stationary X-ray source enclosing a measuring field, said X-ray source comprising a ring-shaped target and media arranged for coaxially guiding the electron beam along a circular path towards said target, and media arranged to deflect the electron beam towards the target for generation of an X-ray bundle that irradiates said measuring field from different directions;

a stationary detector arranged in a ring shape and comprising a plurality of detector elements used for computer generation of an image being examined in said measuring field;

said ring-shaped target comprises a plurality of discrete focal areas arranged such that said plurality of focal areas are discontinuously scanned through respective focal points of the electron beam;

wherein said system is configured for structural connection to a radiation therapy unit to form a single structural unit therewith; and further comprising a radiation therapy unit configured between said ring-shaped target and said ring shaped detector.

5. A computer tomography system, comprising:

at least one stationary electron source configured for generation of an electron beam;

a ring-shaped stationary X-ray source enclosing a measuring field, said X-ray source comprising a ring-shaped target and media arranged for coaxially guiding the electron beam along a circular path towards said target, and media arranged to deflect the electron beam towards the target for generation of an X-ray bundle that irradiates said measuring field from different directions;

a stationary detector arranged in a ring shape and comprising a plurality of detector elements used for computer generation of an image being examined in said measuring field;

said ring-shaped target comprises a plurality of discrete focal areas arranged such that said plurality of focal areas are discontinuously scanned through respective focal points of the electron beam; and wherein said X-ray source, said ring-shaped target, and ring-shaped detector are adjustably attached to each other so as to be adjustable relative to each other and an isocenter of said measuring field.

6. A computer tomography system, comprising:

at least one stationary electron source configured for generation of an electron beam;

a ring-shaped stationary X-ray source enclosing a measuring field, said X-ray source comprising a ring-shaped target and media arranged for coaxially guiding the electron beam along a circular path towards said target, and media arranged to deflect the electron beam towards the target for generation of an X-ray bundle that irradiates said measuring field from different directions;

a stationary detector arranged in a ring shape and comprising a plurality of detector elements used for computer generation of an image being examined in said measuring field;

said ring-shaped target comprises a plurality of discrete focal areas arranged such that said plurality of focal areas are discontinuously scanned through respective focal points of the electron beam; and wherein said ring-shaped target comprises a stepped ring structure with an odd number of saw-toothed elements configured thereon.

7. The computer tomography system as in claim 6, wherein each said saw-toothed element comprises at least one replaceable target element.

8. The computer tomography system as in claim 6, wherein said discrete focal areas are disposed at a lead angle with respect to an axis of the electron beam.

9. The computer tomography system as in claim 6, further comprising a beam delivery tube in which the electron beam rotates in the circular path, and further comprising at least one cooling channel disposed relative to said delivery tube and said ring-shaped target for removing heat generated thereby.

10. The computer tomography system as in claim 6, further comprising means for adjusting the kinetic energy of electrons in the electron beam.

11. The computer tomography system as in claim 6, further comprising an additional stationary electron source for generating a second electron beam, said X-ray source disposed between said electron sources.

12. The computer tomography system as in claim 11, wherein the first and second electron beams are generated at different kinetic energies.

13. The computer tomography system as in claim 11, further comprising an additional detector associated with said additional electron source and second electron beam.

14. The computer tomography system as in claim 6, wherein said ring-shaped target is configured as a double focus ring.

15. The computer tomography system as in claim 6, further comprising an additional X-ray source axially displaced from said X-ray source.

16. The computer tomography system as in claim 6, wherein said ring-shaped target comprises a stepped ring structure with an odd number of saw-toothed elements configured thereon, said guiding media comprising a discrete media associated with each said saw-toothed element.

17. The computer tomography system as in claim 16, wherein said deflecting media comprises electrostatic or magnetic kicker devices associated with each said guiding media.

18. The computer tomography system as in claim 17, wherein said kicker devices are adjustable for changing deflecting angles defined thereby.

19. The computer tomography system as in claim 6, wherein said focal points of the electron beam on said focal areas are adjustable.

20. The computer tomography system as in claim 6, wherein focal points of the electron beam on said focal areas are defined as a line focus to which a line of said detector is assigned.

21. The computer tomography system as in claim 6, wherein focal points of the electron beam on said focal areas are defined as a spring focus to which at least one line of said detector is assigned, whereby the focal points jump in various spots of the line.

22. The computer tomography system as in claim 6, wherein focal points of the electron beam on said focal areas are defined as a spring focus, and further comprising an additional ring-shaped target with individual target elements arranged at a quarter period spacing with respect to said target elements of said first ring-shaped target.

23. The computer tomography system as in claim 6, wherein said detector comprises a scattered ray grid comprising ring lamella.

24. The computer tomography system as in claim 23, further comprising adjustable transversal lamella disposed between said ring lamella in the rotational direction of the electron beam.

25. The computer tomography system as in claim 6, wherein photon fluence is individually adjustable for each said focal area by regulating the stopping time of the electron beam at each said focal area.

26. The computer tomography system as in claim 6, wherein said ring-shaped detector is axially displaced with respect to said ring-shaped target, and further comprising internal shielding between said target and said detector.

27. The computer tomography system as in claim 6, further comprising a torsion-free support frame, wherein other components of said system are arranged within said support frame.

28. The computer tomography system as in claim 6, further comprising a rotatable stand in which other components of said system are supported, said stand rotatable about an axis such that said system is rotatable in a plane parallel to said ring-shaped target.

29. The computer tomography system as in claim 6, further comprising a computer-controlled assembly configured for moving said system within a room.

30. The computer tomography system as in claim 6, wherein said system is configured for structural connection to a radiation therapy unit to form a single structural unit therewith.

* * * * *